United States Patent [19]

Buckler et al.

[11] 4,241,069
[45] Dec. 23, 1980

[54] 3-METHYLENE FLAVANONES AND 3-METHYLENE CHROMANONES

[75] Inventors: Robert T. Buckler, Edwardsburg, Mich.; Frederick E. Ward; David L. Garling, both of Elkhart, Ind.

[73] Assignee: Miles Laboratories, Inc., Elkhart, Ind.

[21] Appl. No.: 72,105

[22] Filed: Sep. 4, 1979

[51] Int. Cl.$^2$ .................. C07D 405/04; A61K 31/35; A61K 31/44; C07D 311/28
[52] U.S. Cl. .................... 424/263; 424/283; 424/275; 260/345.2; 549/60; 546/269
[58] Field of Search ............. 260/345.2; 546/269; 549/60; 424/283, 263, 275

[56] References Cited

U.S. PATENT DOCUMENTS 3,753,985  8/1973  Gavin et al. .................. 260/345.2

Primary Examiner—Alan L. Rotman
Assistant Examiner—Robert T. Bond
Attorney, Agent, or Firm—James D. McNeil

[57] ABSTRACT

Compounds which are 3-methylene flavanones and 3-methylene chromanones having activity against microorganisms are disclosed. The compounds are represented by the general structural formula:

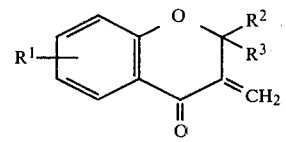

wherein: $R^1$ is a member selected from the group consisting of hydrogen, Br, $CH_3$ and $OCH_3$; $R^2$ is selected from the group consisting of hydrogen and

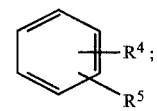

wherein $R^4$ is a member selected from the group consisting of hydrogen, Br, Cl, $CH_3$, $OCH_3$, $NO_2$, $N(CH_3)_3$ and CN; $R^5$ is selected from the group consisting of hydrogen and Cl, with the proviso that when $R^5$ is Cl, $R^4$ is hydrogen or Cl; and $R^3$ is selected from the group consisting of hydrogen, phenyl, 2-thienyl, 4-pyridyl and naphthyl, with the proviso that when $R^3$ is naphthyl, $R^1$ and $R^2$ are hydrogen.

26 Claims, No Drawings

3-METHYLENE FLAVANONES AND 3-METHYLENE CHROMANONES

BACKGROUND OF THE INVENTION

1. Field of the Invention

This invention relates to 3-methylene flavanones and 3-methylene chromanones which exhibit activity against bacteria, yeast or fungi.

2. Prior Art

The prior art discloses numerous derivatives of flavanone (flavone). Flavanone has the following structural formula and is numbered as shown:

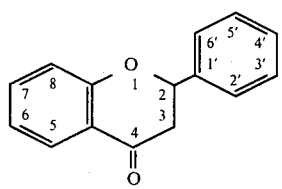

Chromanone has the following structure:

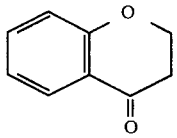

U.S. Pat. No. 3,002,797 discloses flavanone-7-oxy-acetamides. U.S. Pat. No. 3,495,009 discloses antiinflammatory flavanone compounds, unsubstituted at the 3-position, and halogenated in the 4' position. U.S. Pat. No. 3,598,840 discloses the production of flavanones having a hydroxy or acetoxy radical in the 3-position. U.S. Pat. Nos. 3,410,851 and 3,753,985 both assigned to the present assignee, disclose 3-aminomethyl substituted flavanones which are antimicrobial agents.

None of the prior art referred to above discloses flavanone or chromanone antimicrobial compounds having a methylene group at the 3-position.

SUMMARY OF THE INVENTION

The present invention is directed to 3-methylene flavanones and 3-methylene chromanones. The claimed compounds can be represented by general structural formula I as:

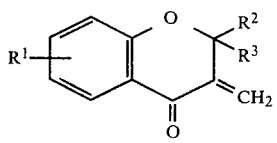

and pharmacologically acceptable, non-toxic salts thereof wherein: $R^1$ is a member selected from the group consisting of hydrogen, Br, $CH_3$ and $OCH_3$; $R^2$ is selected from the group consisting of hydrogen and

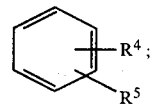

wherein $R^4$ is a member selected from the group consisting of hydrogen, Br, Cl, $CH_3$, $OCH_3$, $NO_2$, $N(CH_3)_2$, $C(CH_3)_3$ and CN; $R^5$ is selected from the group consisting of hydrogen and Cl, with the proviso that when $R^5$ is Cl, $R^4$ is hydrogen or Cl; and $R^3$ is selected from the group consisting of hydrogen, phenyl, 2-thienyl, 4-pyridyl and naphthyl, with the proviso that when $R^3$ is naphthyl, $R^1$ and $R^2$ are hydrogen.

DESCRIPTION OF THE INVENTION

In general, the compounds of the present invention can be conveniently placed in the following three categories:

A. 3-Methylene Flavanones, where $R^3$ is hydrogen;

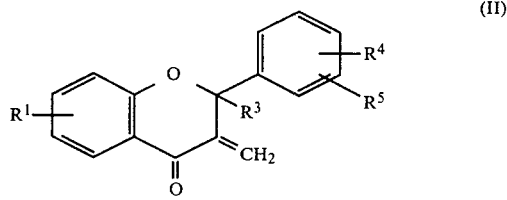

B. 3-Methylene Flavanones, where $R^1$, $R^4$ and $R^5$ are hydrogen and $R^3$ is phenyl, 2-thienyl or 4-pyridyl;

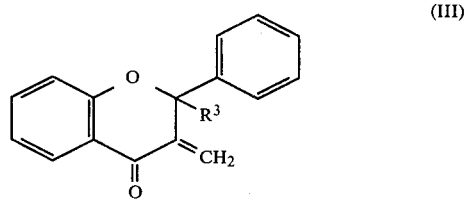

C. 3-Methylene Chromanones, where $R^2$ is hydrogen and $R^3$ is naphthyl;

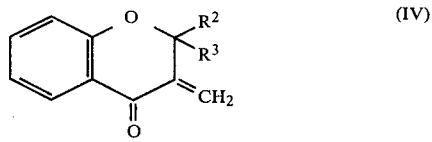

Two methods were used to prepare the 3-methylene flavanones and chromanones. In the first method, the appropriately-substituted 2-hydroxyacetophenones V are condensed with substituted benzaldehydes VI or naphthaldehydes by heating in aqueous ethanol in the presence of a base such as borax or sodium hydroxide to give the corresponding chalcones VII. The 2-hydroxyacetophenones are the products of the Fries rearrangement ("Preparative Organic Chemistry", G. Hilgetag and A. Martini Eds., John Wiley & Sons, New York, New York, 1972, page 1068) and are readily available. In some cases (e.g., Example 14) the chalcones VII spontaneously cyclize to the flavanones VIII. In other cases (e.g., Example 4) the chalcones VII were cyclized to the flavanones VIII by heating them in dilute acid.

The flavanones and chromanones can be converted to the corresponding Mannich bases IX by treatment with formaldehyde, dimethylamine and hydrochloric acid (See B. Reichert "Die Mannich Reaktion", Berlin, 1959, p. 22-24). These Mannich bases decompose on treatment with dilute base (e.g., Example 4) to yield the desired 3-methylene flavanones II and III or desired 3-methylene chromones IV.

Alternately, the flavanones VIII can be converted directly to the 3-methylene flavanones by heating for several hours with the reagent bis-(dimethylamino)methane in acetic anhydride.

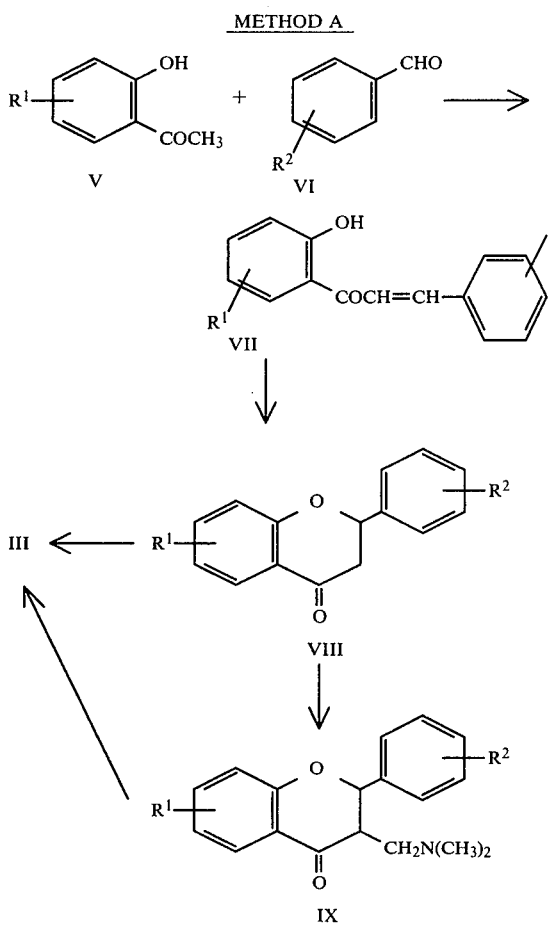

DESCRIPTION OF THE PREFERRED EMBODIMENTS

The following compounds comprise preferred embodiments of Formula III:

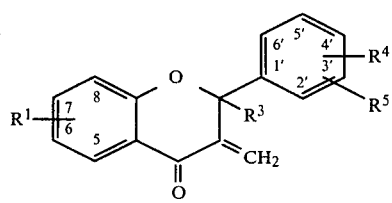

TABLE A

| 3-Methylene Flavanones where $R^3$ is hydrogen | | | | |
|---|---|---|---|---|
| Example No. | TR Number | $R^1$ | $R^4$ | $R^5$ |
| 1 | 3489 | H | H | H |
| 2 | 3667 | H | 3'-Cl | H |
| 3 | 3498 | H | H | 4'-Cl |
| 4 | 3734 | H | 2'-Cl | 4'-Cl |
| 5 | 3671 | H | 3'-Br | H |
| 6 | 3673 | H | 4'-Br | H |
| 7 | 3648 | H | 3'-OCH$_3$ | H |
| 8 | 3762 | H | 4'-OCH$_3$ | H |
| 9 | 3666 | H | 3'-NO$_2$ | H |
| 10 | 3614 | H | 4'-NO$_2$ | H |
| 11 | 3654 | H | 4'-N(CH$_3$)$_2$ | H |
| 12 | 3670 | H | 3'-CH$_3$ | H |
| 13 | 3485 | H | 4'-CH$_3$ | H |
| 14 | 3683 | H | 4'-C(CH$_3$)$_3$ | H |
| 15 | 3665 | H | 3'-CN | H |
| 16 | 3649 | H | 4'-CN | H |
| 17 | 3791 | 6-Br | 4'-Br | H |
| 18 | 3782 | 7-OCH$_3$ | 4'-Cl | H |
| 19 | 3783 | 6-CH$_3$ | H | H |

EXAMPLE 1

3-methylene flavanone

A mixture of 44.8 g (0.2 mol) of flavanone (commercially available from Aldrich Chemical Co., Milwaukee, Wisconsin), 32.6 g (0.4 mole) of dimethylamine hydrochloride, 12.6 g (0.4 mol) of paraformaldehyde, 1 ml of concentrated HCl, and 120 ml of 2-propanol was stirred at reflux for 1 hour. The reaction was then allowed to cool to room temperature, the solvent was removed under reduced pressure and the residue partitioned between 400 ml of ether and 1 liter of 5 percent aqueous hydrochloric acid. The aqueous phase was separated, washed with 200 ml of ether, cooled and made basic with solid K$_2$CO$_3$. The liberated base was extracted into ether, the ether solution dried over anhydrous Na$_2$SO$_4$, filtered and concentrated under reduced pressure. The residue was taken up in 200 ml of ethyl acetate and treated with excess acetyl chloride and ethanol. Upon cooling, white crystals precipitated. After drying, a yield of 43.8 g of 3-dimethylaminomethyl flavanone hydrochloride, (mp 172°-174° C.) was obtained.

Ten grams of this hydrochloride salt was dissolved in 400 ml of H$_2$O and heated on the steam bath for 2 hours. After cooling to room temperature, the cloudy solution was extracted with ether. The ether solution was dried over anhydrous Na$_2$SO$_4$, filtered and evaporated under reduced pressure to give 2.2 g of an oil. The oil was taken up in hot petroleum ether (b.p. 30° C.), filtered, and concentrated to a 10 ml volume. After cooling to room temperature, the solution was decanted from a small amount of gummy precipitate. Evaporation of the solution gave 300 mg of a yellow oil of 3-methylene flavanone.

NMR Spectrum (CCl$_4$): δ 5.05 (1H, t, J=2 Hz); 5.85 (1H, t, J=2 Hz); 6.3 (1H, t, J=2 Hz).

Mass Spectrum (70 eV) m/e: 236 (M+).

Infrared Spectrum (CCl$_4$): 1670 cm$^{-1}$ (νco).

EXAMPLE 2

3'-chloro-3-methylene flavanone

3'-Chloro flavanone was prepared as described in J. Taiwan Pharm. Assoc. 3, 39 (1951) and Chem Abst. 49, 2432 g (1955). A 18.5 g (0.072 mol) portion of 3'-chloro flavanone was converted to 9.9 g of 3'-chloro-3-dimethylaminomethyl flavanone hydrochloride (m.p. 109°–151° C.) in a similar manner as described in Example 1.

Calcd for $C_{18}H_{18}ClNO_2 \cdot HCl$: C, 61.37; H, 5.44; N, 3.98. Found: C, 61.19; H, 5.37; N, 3.86.

A mixture of 1.76 g (5 mmol) of this hydrochloride salt and 12 ml of bis-(dimethylamino)methane (commercially available from Aldrich Chemical Co.) was stirred under argon at room temperature; 8 ml of acetic anhydride was added dropwise. A transient rise in temperature occurred, which was stopped by immersing the reaction vessel in a cooling bath. After 20 minutes, an additional 4 ml portion of acetic anhydride was added. The reaction mixture was then poured into 100 g of crushed ice and extracted with ether. The ether phase was separated, washed with sodium bicarbonate solution, dried over anhydrous $Na_2SO_4$, filtered and evaporated to give 1.5 g of a yellow oil. The oil was chromatographed on 100 g of silica gel and eluted with benzene to yield 1 g of a pale yellow waxy solid of 3'-chloro-3-methylene flavanone, m.p. 85°–88° C.

NMR spectrum ($CDCl_3$): $\delta$ 5.2 (1H, m); 6.0 (1H, m); 6.5 (1H, m). Mass spectrum (70 eV) m/e: Calcd for $C_{16}H_{11}ClO_2$: 270.04469. Found: 270.0421 (M+).

Infrared Spectrum ($CHCl_3$): 1675 cm$^{-1}$ ($\nu_{co}$).

EXAMPLE 3

4'-chloro-3-methylene flavanone

In a similar manner as described in Example 1, 10 g of 4'-chloro flavanone, as described in Bull. Soc. Chim. France 2248 (1963), was converted to 4.0 g of crude 4'-chloro-3-dimethylaminomethyl flavanone hydrochloride. The hydrochloride salt was recrystallized twice from acetone to give 1.1 g of crystals, m.p. 147°–149° C.

Calcd. for $C_{18}H_{18}ClNO_2 \cdot HCl$: C, 61.37; H, 5.44; N, 3.98. Found: C, 61.88; H, 5.58; N, 4.12.

The combined filtrates from the above recrystallizations were mixed with $H_2O$ and stirred for one hour. An oil separated that later crystallized. The crystals were filtered and recrystallized from petroleum ether to give 500 mg of the desired flavanone as a white solid, m.p. 84°–85° C.

Calcd for $C_{16}H_{11}ClO_2$: C, 70.98; H, 4.10. Found: C, 70.56; H, 4.23.

NMR spectrum ($CCl_4$): $\delta$ 5.1 (m, 1H), 5.90 (m, 1H), 6.3 (m, 1H).

EXAMPLE 4

2',4'-dichloro-3-methylene flavanone

2-Hydroxy-2',4'-dichlorochalcone, as described in Arch. Pharm. 295, 16 (1962), was cyclized to the flavanone by the procedure described in Bull. Soc. Chem. France 674 (1973). Two recrystallizations from methanol gave 3 g of 2',4'-dichloro flavanone as pale tan crystals, m.p. 91°–92° C.

Calcd. for: $C_{15}H_{10}Cl_2O_2$: C, 61.46; H, 3.44. Found: C, 61.42; H, 3.46.

A mixture of 3 g (10 mmol) of the 2',4'-dichloro flavanone and 27 ml of bis-(dimethylamino)methane was stirred at room temperature; 27 ml of acetic anhydride was added dropwise over 15 minutes. A slight temperature rise occurred. One hour later the reaction was partitioned between 200 ml of ether and 200 ml of cold $H_2O$. The aqueous phase was separated, washed with two 250 ml portions of ether, and discarded. The combined ether extracts were washed with saturated aqueous $NaHCO_3$ solution, dried over anhydrous $Na_2SO_4$, filtered and evaporated. The residual oil was chromatographed on 200 g of silica gel, eluting with benzene. This gave 2.5 g of 2',4'-dichloro-3-methylene flavanone, isolated as a solid, m.p. 86°–87° C.

Calcd. for $C_{16}H_{10}Cl_2O_2$: C, 62.97; H, 3.30. Found: C, 63.20; H, 3.36.

NMR Spectrum ($CCl_4$): $\delta$ 4.9 (1H, m), 6.3 (2H, m).

EXAMPLE 5

3'-bromo-3-methylene flavanone

In a similar manner as described in Example 1, 17 g of 3'-bromo flavanone, as described in J. Chinese Chem. Soc. 11, 102 (1964); ibid. 10, 125 (1963) and Chem. Abst. 62, 6011b (1965), was converted to 6.7 g of the hydrochloride salt of 3'-bromo-3-dimethylaminomethyl flavanone, as white crystals, m.p. 105°–172° C.

Calcd. for $C_{18}H_{18}BrNO_2 \cdot HCl$: C, 54.49; H, 4.83, N, 3.53. Found: C, 54.27; H, 4.93; N, 3.79.

A 1.91 g portion of this hydrochloride salt was converted to 1.3 g of 3'-bromo-3-methylene flavanone, m.p. 98°–100° C., using the procedure described in Example 2.

Calcd. for $C_{16}H_{11}BrO_2$: C, 60.97; H, 3.52. Found: C, 60.80; H, 3.56.

NMR Spectrum ($CDCl_3$): $\delta$ 5.3 (1H, m), 6.0 (1H, m), 6.5 (1H, m).

EXAMPLE 6

4'-bromo-3-methylene flavanone

In a similar manner as described in Example 1, 11.8 g of 4'-bromo flavanone, as described in J. Taiwan Pharm. Assoc. 3, 39 (1951) and Chem. Abst. 49, 2432 g (1955), was converted to 4.2 g of the hydrochloride salt of 4'-bromo-3-dimethylaminomethyl flavanone, m.p. 157°–159° C.

Calcd. for $C_{18}H_{18}BrNO_2 \cdot HCl$: C, 54.49; H, 4.83; N, 3.53. Found: C, 54.42; H, 4.93; N, 3.63.

A 1.91 g portion of this hydrochloride salt was converted to 1.28 g of 4'-bromo-3-methylene flavanone, m.p. 91°–92° C., using the procedure described in Example 2.

Calcd. for $C_{16}H_{11}BrO_2$: C, 60.97; H, 3.52. Found: C, 61.05; H, 3.42.

NMR Spectrum ($CDCl_3$): $\delta$ 5.1 (1H, m), 5.9 (1H, m), 6.4 (1H, m).

EXAMPLE 7

3'-methoxy-3-methylene flavanone

In a similar manner as described in Example 1, 25 g of 3'-methoxy flavanone, as described in Chem. Ber. 38, 933 (1905), was converted to the hydrochloride salt of 3'-methoxy-3-dimethylaminomethyl flavanone, m.p. 155°–156° C., 3.65 g, recrystallized from ethyl acetate.

Calcd. for $C_{19}H_{21}NO_3 \cdot HCl$: C, 65.61; H, 6.38; N, 4.03. Found: C, 65.31; H, 6.62; N, 4.21.

The filtrate from the crystallization was evaporated to give 2 g of an oil. This was partitioned between ether and saturated aqueous $NaHCO_3$ solution. The ether phase was separated, dried over anhydrous $Na_2SO_4$, filtered, and evaporated. The oily residue was taken up in 10 ml of methanol and 5 ml of methyl iodide and allowed to stand for several days. The solvent was then removed and the gummy solid residue was partitioned between ether and 10 percent NaOH solution. The ether phase was separated, dried over anhydrous $Na_2SO_4$, filtered and concentrated to give 700 mg of an oil.

The oil was taken back up in ether and washed with 5 percent HCl solution, H$_2$O, then dried over anhydrous Na$_2$SO$_4$, filtered and evaporated to give 480 mg of solid. The solid was taken up in benzene and purified by preparative thin-layer chromatography (tlc); the silica gel tlc plates were manufactured by E. Merck & Co., Darmstadt, Germany. 200 Mg of the desired product, 3'-methoxy-3-methylene flavanone, was obtained.

NMR Spectrum (CCl$_4$): δ 5.1 (1H, m), 5.9 (1H, m), 6.3 (1H, m).

Mass Spectrum (70 eV) m/e: Calcd. for C$_{17}$H$_{14}$O$_3$: 266.0930. Found: 266.0937 (M+).

Infrared Spectrum (CCl$_4$): 1680 cm$^{-1}$ ($\nu$co).

EXAMPLE 8

4'-methoxy-3-methylene flavanone

In a similar manner as described in Example 1, 27.6 g of 4'-methoxy flavanone prepared as described in *Acta Phytochem.* 2, 99 (1925) and *Chem. Abst.* 20, 2162 (1926) was converted to 2.85 g of the hydrochloride salt of 4'-methoxy-3-dimethylaminomethyl flavanone, m.p. 149°-151° C.

Calcd. for C$_{19}$H$_{21}$NO$_3$.HCl: C, 65.61; H, 6.38; N, 4.03. Found: C, 65.40; H, 6.46; N, 4.06.

2.0 g of the hydrochloride salt was converted to 1.44 g of 4'-methoxy-3-methylene flavanone, isolated as a yellow oil, using the procedure described in Example 2.

NMR Spectrum (CCl$_4$): δ 5.1 (1H, m), 5.9 (1H, m), 6.3 (1H, m).

Mass Spectrum (70 eV) m/e: Calcd. for C$_{17}$H$_{14}$O$_3$: 266.0939. Found: 266.09161 (M+).

Infrared Spectrum (CCl$_4$): 1685 cm$^{-1}$ ($\nu$co).

EXAMPLE 9

3'-nitro-3-methylene flavanone

A mixture of 1.35 g (5 mmol) of 3'-nitroflavanone [prepared as described in *J. Chem. Soc. Japan, Pure Chem. Sect.* 74, 827 (1953)], and 12 ml of bis-(dimethylamino)methane was stirred at room temperature; 12 ml of acetic anhydride was added dropwise over 15 minutes. The temperature rose to 77°. After cooling to ambient temperature, the reaction was partitioned between 100 ml portions of ether and 100 ml portions of cold water. The aqueous phase was separated, washed with two 100 ml of ether, and discarded. The combined ether extracts were washed with saturated aqueous NaHCO$_3$ solution, dried over anhydrous Na$_2$SO$_4$, filtered and evaporated. The residual oil was chromatographed on 100 g of silica gel, eluting with benzene to yield 548 mg of 3'-nitro-3-methylene flavanone, isolated as a white solid, m.p. 131°-132° C.

NMR Spectrum (CDCl$_3$): δ 5.3 (1H, m), 6.2 (1H, m), 6.6 (1H, m).

Mass Spectrum (70 eV) m/e: Calcd. for C$_{16}$H$_{11}$NO$_4$: 281.06873. Found: 281.068700 (M+).

Infrared Spectrum (CDCl$_3$): 1680 cm$^{-1}$ ($\nu$co).

EXAMPLE 10

4'-nitro-3-methylene flavanone

A mixture of 18.1 g (67 mmol) of 4'-nitro flavanone, prepared as described in *J. Chem. Soc. Japan, Pure Chem. Sect.* 74, 827 (1953), 4.04 g (134 mmol) of paraformaldehyde, 10.97 g (134 mmol) of dimethylamine hydrochloride, 1 ml of concentrated HCl, and 200 ml of 2-propanol was refluxed for three hours. When cool, the solvent was removed under reduced pressure and the residue partitioned between CHCl$_3$ and 5 percent aqueous HCl. The layers were separated and the organic layer was washed with 3-100 ml portions of 5 percent HCl. The combined aqueous extracts were neutralized with solid Na$_2$CO$_3$ and extracted with ether. The ether was dried over anhydrous Na$_2$SO$_4$, filtered, and concentrated. The oily residue was dissolved in ethyl acetate and treated with 1 ml of ethanol and 1.5 ml of acetyl chloride. The solvent was then evaporated to give a glassy residue. This was taken up in 500 ml of hot ethyl acetate containing 20 ml of acetone and cooled. A precipitate formed that was recrystallized from methanol to give 810 mg of 4'-nitro-3-methylene flavanone as a solid, m.p. 135°-136° C.

Calcd. for C$_{16}$H$_{11}$NO$_4$: C. 68.31; H, 3.94; N, 4.98. Found: C, 67.68; H, 3.98; N, 5.09.

NMR Spectrum (CDCl$_3$): δ 5.3 (s, 1H), 6.2 (s, 1H), 6.5 (s, 1H).

EXAMPLE 11

4'-dimethylamino-3-methylene flavanone

In a similar manner as described in Example 1, 16.5 g of 4'-dimethylamino flavanone, prepared as described in *J. Chem. Soc. Japan, Pure Chem. Sect.* 74, 827 (1953), was converted to 2.6 g of the hydrochloride salt of 4'-dimethylamino-3-dimethylaminomethyl flavanone, recrystallized from alcohol, m.p. 184°-186° C.

Calcd. for C$_{20}$H$_{24}$N$_2$O$_2$.HCl: C, 66.56; H, 6.98; N, 7.76. Found: C, 66.27; H, 7.11; N, 7.53.

The filtrates from the recrystallization of the HCl salt were evaporated under reduced pressure. The oily residue was partitioned between 200 ml each of H$_2$O and ether. The ether phase was separated, dried over anhydrous Na$_2$SO$_4$, filtered and evaporated. This residue was extracted twice with 250 ml portions of boiling pentane, and the combined extracts cooled in the refrigerator. A yellow precipitate formed that was separated and recrystallized from CHCl$_3$-petroleum ether to give 1.5 g of 4'-dimethylamino-3-methylene flavanone as a solid, m.p. 110°-112° C.

Calcd for C$_{18}$H$_{17}$NO$_2$: C, 77.39; H, 6.13; N, 5.01. Found: C, 76.16; H, 7.25; N, 5.25.

NMR Spectrum (CDCl$_3$): δ 2.9 (s, 6H), 5.3 (d, 1H, J=4 Hz), 5.4 (d, 1H, J=4 Hz).

Mass Spectrum (70 eV) m/e: Calcd. for C$_{18}$H$_{17}$NO$_2$: 279.1255. Found: 279.1269 (M+).

EXAMPLE 12

3'-methyl-3-methylene flavanone

A mixture of 3-methylbenzaldehyde (12 g, 0.1 mol), 2-hydroxyacetophenone (13.6 g, 0.1 mol), and 2 liters of 0.1 N NaOH was stirred at room temperature for 4 days. The reaction was extracted with ether and the ether dried and evaporated to give 20.5 g of 3'-methyl flavanone as an oil. The oil, not further purified but used directly, was converted in a similar manner as described in Example 1 into 8.2 g of the hydrochloride salt of 3'-methyl-3-dimethylaminomethyl flavanone, as a solid, m.p. 156°-158° C.

Calcd. for C$_{19}$H$_{21}$NO$_2$.HCl: C. 68.77; H, 6.68; N, 4.22. Found: C. 67.84; H, 6.31; N, 4.22.

1.66 g of this hydrochloride salt was converted to 230 mg of 3'-methyl-3-methylene flavanone, isolated as an oil, using the procedure described in Example 2.

NMR Spectrum (CDCl$_3$): δ 2.4 (3H, s), 5.2 (1H, m), 6.0 (1H, m), 6.4 (1H, m).

Mass Spectrum (70 eV) m/e: Calcd: for C$_{17}$H$_{14}$O$_2$: 250.09930. Found: 250.09953 (M+).

Infrared Spectrum (CHCl$_3$): 1680 cm$^{-1}$ ($\nu$co).

EXAMPLE 13

4'-methyl-3-methylene flavanone

A mixture of 12 g (0.1 mol) of 4-methylbenzaldehyde, 13.6 g (0.1 mol) of 2-hydroxyacetophenone, 250 ml of ethanol, and 250 ml of $H_2O$ containing 38.1 g (0.1 mol) of sodium borate was refluxed overnight. It was cooled, concentrated under reduced pressure, and the residue extracted with $CHCl_3$. The $CHCl_3$ was dried over anhydrous $Na_2SO_4$, filtered, and evaporated to give a mixture from which was extracted 13.6 g of impure 4'-methyl flavanone [See German Offen. No. 2,535,338 (17 Feb. 1977)]. The material was not further purified but was converted directly, in a similar manner as described in Example 1, to the HCl salt of 4'-methyl-3-dimethylaminomethyl flavanone, as a solid recrystallized from methanol-ethyl acetate, m.p. 167°–169° C.

Calcd. for $C_{19}H_{12}NO_2 \cdot HCl$: C, 68.77; H, 6.68; N, 4.22. Found: C, 68.74; H, 6.76; N, 4.28.

The filtrates from the recrystallization of the HCl salt were evaporated under reduced pressure and the residue treated with boiling ethyl acetate. The ethyl acetate solution was cooled, filtered, and evaporated to give an orange oil. It was treated in the manner of Example 7 to give 450 mg of 4'-methyl-3-methylene flavanone isolated as an oil.

Calcd. for $C_{17}H_{14}O_2$: C, 81.58; H, 6.64. Found: C, 81.09; H, 5.68.

NMR Spectrum ($CCl_4$): δ 2.4 (s, 3H), 5.2 (m, 1H), 5.9 (m, 1H), 6.4 (m, 1H).

EXAMPLE 14

4'-t-butyl-3-methylene flavanone

A mixture of 22.7 g (0.14 mol) of 4-t-butylbenzaldehyde, 19 g (0.14 mol) of 2-hydroxyacetophenone, 38 g (0.1 mol) of borax, 250 ml of $H_2O$ and 150 ml of ethanol was refluxed for one day. The reaction was cooled and diluted with an equal volume of $H_2O$ and extracted with ether. The ether was washed with brine, dried over anhydrous $Na_2SO_4$, filtered, and evaporated to give a brown oil. The oil was chromatographed on 1200 g of silica gel, eluting with benzene. The desired product was obtained as an oil. Recrystallization from petroleum ether gave 2.8 g of 4'-t-butyl flavanone as white crystals, m.p. 103°–104° C.

Calcd. for $C_{19}H_{20}O_2$: C, 81.39; H, 7.19. Found: C, 81.26; H, 6.88.

In a similar manner as described in Example 4, 1.40 g of this flavanone was converted to 112 mg of 4'-t-butyl-3-methylene flavanone, isolated as a pale yellow solid, m.p. 104°–109° C.

NMR Spectrum ($CDCl_3$): δ 1.3 (9H, s), 5.2 (1H, m), 5.9 (1H, m), 6.4 (1H, m).

Mass Spectrum (70 eV) m/e: Calcd. for $C_{20}H_{20}O_2$: 292.14622. Found: 292.15531 (M+).

Infrared Spectrum ($CHCl_3$): 1680 cm$^{-1}$ ($\nu$co).

EXAMPLE 15

3'-cyano-3-methylene flavanone

A mixture of 3-cyanobenzaldehyde (25 g, 0.19 mol), 2-hydroxyacetophenone (25.9 g. 0.19 mol), 38.1 g (0.1 mol) of borax, 250 ml of ethanol, and 250 ml of $H_2O$ was refluxed for four days. When cool the reaction mixture was diluted with $H_2O$ and extracted with ethyl acetate. The ethyl acetate was dried over anhydrous $Na_2SO_4$, filtered, and evaporated to give a dark, tarry residue. The residue was chromatographed on 1 kg of silica gel, eluting with benzene. From this was isolated 5 g of 3'-cyano flavanone as an oil.

NMR Spectrum ($CDCl_3$): δ 2.95 and 3.0 (s and d, 2H, J=2 Hz) and δ 5.45 and 5.60 (d and d, d, J=6 Hz and 10 Hz).

Infrared Spectrum ($CHCl_3$): 1690 cm$^{-1}$ ($\nu$co), 2240 cm$^{-1}$ ($\nu$cn).

The flavanone was not purified further, but in a similar manner as described in Example 1 was converted to 1.0 g of the hydrochloride salt of 3'-cyano-3-dimethylaminomethyl flavanone as a solid, m.p. 104°–106° C. after recrystallization from 2-propanol-ethyl acetate-petroleum ether.

Calcd. for $C_{19}H_{18}N_2O_2 \cdot HCl$: C, 66.56; H, 5.59; N, 8.17. Found: C, 65.82; H, 6.08; N, 7.74.

The mother liquors from the recrystallization of the hydrochloride salt were evaporated and the residue taken up in 500 ml $H_2O$ and allowed to stand for 1 day. It was extracted twice with ethyl acetate and the extracts dried over anhydrous $Na_2SO_4$. It was filtered and evaporated, and the residue purified by preparative tlc to yield 430 mg of the desired 3'-cyano-3-methylene flavanone as an oil.

NMR Spectrum ($CDCl_3$): δ 5.2 (1H, m), 6.0 (1H, m), 6.4 (1H, m).

Mass Spectrum (70 eV) m/e: Calcd. for $C_{17}H_{11}NO_2$: 261.0787. Found: 261.0793 (M+).

Infrared Spectrum ($CDCl_3$): 1680 cm$^{-1}$ ($\nu$co), 2230 ($\nu$cn).

EXAMPLE 16

4'-cyano-3-methylene flavanone

In a similar manner as described in Example 1, 4.72 g of 4'-cyano flavanone, produced as described in *Bull. Soc. Chim. France* 2248 (1963), was converted to 1.2 g of the hydrochloride salt of 4'-cyano-3-dimethylaminomethyl flavanone, m.p. 118°–132° C.

Calcd. for $C_{19}H_{18}N_2O_2 \cdot HCl$: C, 66.56; H, 5.59; N, 8.17. Found: C, 65.18; H, 5.94; N, 8.12.

The filtrate from the recrystallization of the hydrochloride salt (2-propanol and ether) was treated in the manner of Example 7 to give 200 mg of 4'-cyano-3-methyleneflavanone as an oil.

NMR Spectrum ($CDCl_3$): δ 5.3 (m, 1H), 6.1 (m, 1H), 6.5 (m, 1H).

Mass Spectrum (70 eV) m/e: Calcd. for $C_{17}H_{11}NO_2$: 261.0787. Found: 261.0768 (M+).

Infrared Spectrum ($CHCl_3$): 1680 cm$^{-1}$ ($\nu$co), 2230 cm$^{-1}$ ($\nu$cn).

EXAMPLE 17

4',6-dibromo-3-methylene flavanone

A mixture of 25 g (0.135 mol) of 4-bromobenzaldehyde, 29 g (0.135 mol) of 5-bromo-2-hydroxyacetophenone, 51.5 g (0.135 mol) of borax, 180 ml of ethanol, and 300 ml of $H_2O$ was refluxed for one day. The reaction mixture was cooled, diluted with an equal volume of $H_2O$ and extracted with ether. The ether was dried over anhydrous $Na_2SO_4$, filtered, and evaporated. This gave 6.67 g of 4',6-dibromo flavanone as a pale yellow solid, m.p. 167°–168° C.

Calcd. for $C_{15}H_{10}Br_2O_2$: C, 47.15; H, 2.64. Found: C, 47.25; H, 2.73.

In a similar manner as described in Example 4, 3.3 g of this flavanone was converted to 2.6 g of 4',6-dibromo-3-methylene flavanone, isolated as a pale yellow solid, m.p. 115°–117° C.

Calcd. for $C_{16}H_{10}Br_2O_2$: C, 48.76; H, 2.56. Found: C, 49.09; H, 2.67.

NMR Spectrum (CDCl$_3$) δ 5.2 (m, 1H), 5.9 (m, 1H), 6.4 (m, 1H).

EXAMPLE 18

4'-chloro-7-methoxy-3-methylene flavanone

A mixture of 20 g (0.120 mol) of 2-hydroxy-4-methoxy acetophenone, 16.9 g (0.120 mol) of 4-chlorobenzaldehyde, 45.8 g (0.120 mol) of borax, 150 ml of ethanol, and 250 ml of H$_2$O was refluxed for one day. When cool, the reaction was diluted with an equal volume of H$_2$O and extracted with ether, then CHCl$_3$. The organic extracts were combined, dried over anhydrous Na$_2$SO$_4$, and evaporated. The residue was chromatographed on 1200 g of silica gel 60, eluting with a gradient of benzene to 19:1 v:v benzene:MeOH. This gave 3.2 g of 4'-chloro-7-methoxy flavanone as a white solid, m.p. 121°-122° C.

Calcd. for $C_{16}H_{13}ClO_3$: C, 66.56; H, 4.54. Found: C, 66.76; H, 4.52.

In a similar manner as described in Example 4, 2.61 g of this flavanone was converted to 1.16 g of 4'-chloro-7-methoxy-3-methylene flavanone, isolated as a white solid, m.p. 97°-99° C.

NMR Spectrum (CDCl$_3$): δ 3.8 (s, 3H), 5.2 (m, 1H), 5.9 (m, 1H).

Mass Spectrum (70 eV) m/e: Calcd. for $C_{17}H_{13}ClO_3$: 300.05524. Found: 300.05700 (M+).

Infrared Spectrum (CHCl$_3$): 1680 cm$^{-1}$ (νco).

EXAMPLE 19

6-methyl-3-methylene flavanone

In a similar manner as described in Example 4, 4 g of 6-methyl flavanone, prepared as described in *Justus Liebig's Ann.* 587, 1 (1954), was converted to 1.82 g of 6-methyl-3-methylene flavanone, isolated as a white solid, m.p. 57°-63° C.

Calcd. for $C_{17}H_{14}O_2$: C, 81.58; H, 5.64. Found: C, 81.25; H, 5.76.

The following compounds comprise preferred embodiments of Formula III:

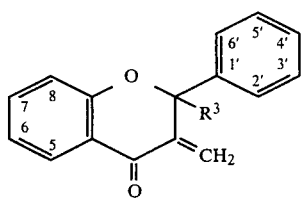

TABLE B

3-Methylene Flavanones where $R^1$, $R^4$ and $R^5$ are hydrogen and $R^3$ is phenyl, 2-thienyl or 4-pyridyl

| Example No. | TR Number | $R^3$ |
|---|---|---|
| 20 | 3742 | phenyl |
| 21 | 3928 | 2-thienyl |
| 22 | 3927 | 4-pyridyl |

EXAMPLE 20

3-methylene-2-phenyl flavanone

In a similar manner as described in Example 4, 4 g of 2-phenyl flavanone, prepared as described in *Chem. Ber.* 94, 241 (1961), was converted to 1.30 g of 3-methylene-2-phenyl flavanone, m.p. 165°-167° C., after recrystallization from petroleum ether.

Calcd. for $C_{22}H_{16}O_2$: C, 84.59; H, 5.16. Found: C, 84.70; H, 5.16.

NMR Spectrum (CDCl): δ 5.0 (m, 1H), 6.6 (m, 1H).

EXAMPLE 21

3-Methylene-2-(2-thienyl) flavanone

A mixture of 56.5 g (0.3 mol) of commercially available 2-benzoylthiophene, 24.4 g (0.217 mol) potassium-t-butoxide, 25 ml t-butanol, and 200 ml toluene was heated to reflux, and a solution of 4 g (0.0294 mol) 2-hydroxyacetophenone in 75 ml toluene was added dropwise with stirring. After heating overnight, the mixture was allowed to stir 3 days at room temperature; a black tar formed. The black tar was partitioned between 500 ml 2:1 toluene:ether and 500 ml 1:1 10 percent acetic acid:concentrated hydrochloric acid. The combined organic layers were washed with brine and dried over sodium sulfate. Filtration and solvent removal left a black tarry residue which was chromatographed on 2 kg of silica gel, eluting with toluene. A 2.4 g portion of a golden brown oil, a mixture of the E- and Z-isomers of 2'-hydroxy-2-(2-thienyl)chalcone, was obtained.

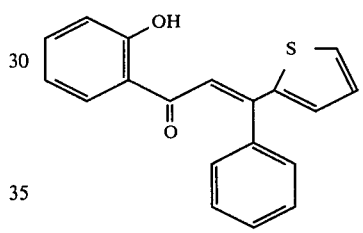

E-isomer

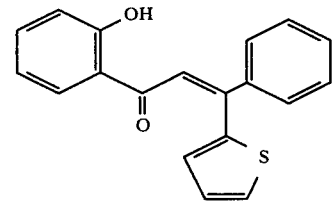

Z-isomer

The chalcone mixture was not further purified but was refluxed overnight in 200 ml of glacial acetic acid containing 50 ml of conc. HCL. Evaporation gave an oil that was chromatographed on 75 g of silica gel, eluting with toluene. A 1.7 g portion of 2-(2-thienyl) flavanone was isolated as a tan solid, mp 78°-80° C.

Analysis: Calcd. for $C_{19}H_{14}SO_2$: C, 74.48; H, 4.75. Found: C, 75.39; H, 4.71.

In a similar manner as described in Example 4, 1.5 g of this flavanone was converted to 1.15 g of 3-methylene-2-(2-thienyl) flavanone, isolated as a tan solid, mp 164°-166° C.

Analysis: NMR Spectrum (CDCl$_3$): δ 5.3 (m, 1H), 6.6 (m, 1H).

Mass Spectrum (70 eV) m/e: Infrared Spectrum (CHCl$_3$): 1680 cm$^{-1}$ (νco).

Calcd. for $C_{20}H_{14}O_2S$: 318.0714. Found: 318.0716.

EXAMPLE 22

3-Methylene-2-(4-pyridyl) flavanone

A mixture of 10.1 g (0.055 mol) of commercially available 4-benzoylpyridine, 10 ml of t-butanol, 50 ml of dry toluene, and 6.17 g (0.055 mol) of potassium t-butoxide was heated to reflux. A solution of 5 g (0.0367 mol) 2-hydroxyacetophenone in 10 ml dry toluene was added dropwise with stirring, and the mixture refluxed overnight. After cooling, the mixture was partitioned between 250 ml of 2:1 toluene:ether and 250 ml of 1:1 (v:v) 10 percent acetic acid:concentrated hydrochloric acid. The aqueous phases were then extracted with chloroform, and the combined chloroform extracts washed with saturated aqueous sodium bicarbonate solution, brine, and dried over sodium sulfate. Filtration and solvent removal left 7.6 g of dark brown oil, which was chromatographed on 250 g of silica gel, eluting with 3:1 v:v chloroform:ethyl acetate. This gave 1.42 g of 2-(4-pyridyl) flavanone as a pale yellow solid, mp 123°–130°.

In a similar manner as described in Example 4, 890 mg of this flavanone was converted to 525 mg of 3-methylene-2-(4-pyridyl) flavanone, isolated as a white solid, mp 159°–160° C.

Analysis: NMR Spectrum (CDCl$_3$): δ 5.0 (m, 1H), 6.4 (m, 1H).

Mass Spectrum (70 eV) m/e: Calcd. for C$_{21}$H$_{15}$NO$_2$: 313.1102. Found: 313.1100.

Infrared Spectrum (CHCl$_3$): 1675 cm$^{-1}$ ($\nu$co).

The following compounds comprise preferred embodiments of Formula IV:

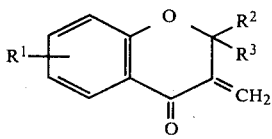

TABLE C

3-Methylene Chromanones where R$^1$ and R$^2$ are hydrogen and R$^3$ is naphthyl

| Example No. | TR Number | R$^3$ |
|---|---|---|
| 23 | 3659 | 1-naphthyl |
| 24 | 3658 | 2-naphthyl |

EXAMPLE 23

3-methylene-2-(1-naphthyl) chromanone

In a similar manner as described in Example 1, 33.4 g of 2-(1-naphthyl) chromanone, as described in *J. Indian Chem. Soc.* 49, 573 (1972), was converted to 9.8 g of the hydrochloride salt of 3-dimethylaminomethyl-2-(1-naphthyl) chromanone, isolated as a solid, m.p. 176°–178° C., after crystallization from ethanol-ethyl acetate.

Calcd. for C$_{22}$H$_{21}$NO$_2$.HCl: C, 71.82; H, 6.03; N, 3.81. Found: C, 71.96; H, 6.23; N, 3.88.

A 450 ml portion of water was added to 2 g of the compound and stirred for three days, the compound was then extracted with ethyl acetate. The ethyl acetate extract was dried over anhydrous Na$_2$SO$_4$, filtered and evaporated to give 1.0 g of 3-methylene-2-(1-naphthyl) chromanone as a solid, m.p. 140°–141° C.

NMR Spectrum (CDCl$_3$): δ 5.0 (m, 1H), 6.4 (m, 1H), 6.6 (m, 1H).

Mass Spectrum (70 eV) m/e: Calcd. for C$_{20}$H$_{14}$O$_2$: 286.0990. Found: 286.1021 (M+).

Infrared Spectrum (CHCl$_3$): 1675 cm$^{-1}$ ($\nu$co).

EXAMPLE 24

3-methylene-2-(2-naphthyl) chromanone

A mixture of 15.6 g (0.1 mol) of 2-naphthaldehyde, 13.6 g (0.1 mol) of 2-hydroxyacetophenone, 38.1 g (0.1 mol) of borax, 250 ml of H$_2$O, and 150 ml of ethanol was refluxed for 4 days. The mixture was cooled, diluted with H$_2$O and extracted with ethyl acetate. The ethyl acetate solution was dried over anhydrous Na$_2$SO$_4$, filtered, and evaporated to give 31 g of an oil consisting chiefly of 2-(2-naphthyl) chromanone. The oil, not further purified but used directly, was converted in a similar manner as described in Example 1 into 4.13 g of the hydrochloride salt of 3-dimethylaminomethyl-2-(2-naphthyl) chromanone, isolated as a solid, m.p. 125°–145° C., after recrystallization from acetone.

Calcd. for C$_{22}$H$_{20}$NO$_2$.HCl: C, 71.82; H, 6.03; N, 3.81. Found: C, 70.90; H, 6.15; N, 3.61.

The mother liquors from the crystallization of the hydrochloride salt were evaporated to give a solid residue. The residue was partitioned between ethyl acetate and aqueous NaHCO$_3$ solution. The organic phase was separated, dried over anhydrous Na$_2$SO$_4$, filtered and evaporated to give 4 g of an oil. It was taken up in 20 ml of methanol and 20 ml of methyl iodide and allowed to stand at room temperature for 3 days. The solution was then evaporated and the residue partitioned between ether and 10 percent aqueous NaOH solution. The ether layer was separated, and the aqueous phase was extracted twice with 100 ml portions of ethyl acetate. The combined organic extracts were washed with H$_2$O, 2 percent HCl, H$_2$O, then dried over anhydrous Na$_2$SO$_4$. Evaporation gave an oil that was chromatographed on 400 g of silica gel, eluting with benzene. This gave 1.15 g of 3-methylene-2-(2-naphthyl) chromanone as a solid, m.p. 95°–98° C.

NMR Spectrum (CDCl$_3$): δ 5.2 (m, 1H), 6.2 (m, 1H), 6.5 (m, 1H).

Mass Spectrum (70 eV) m/e: Calcd. for C$_{20}$H$_{14}$O$_2$: 286.0990. Found: 286.0989 (M+).

Infrared Spectrum (CHCl$_3$): 1675 cm$^{-1}$ ($\nu$co).

Pharmacological Evaluation

The compounds of the present invention were tested for their ability to inhibit the growth of microorganisms by in vitro tests. Generally the in vitro tests involve growing representative microorganisms under conditions favorable to such growth and measuring the effectiveness of one or more compounds in inhibiting or destroying the growth of the microorganisms. The microorganisms used include representative bacteria, fungi and yeasts.

Compounds which are effective against microorganisms in the above described in vitro tests may be effective when applied to living tissue or when applied to inanimate objects. The rate of application of a compound effective against a microorganism is dependent upon the potency and efficacy of the compound. Determination of the rate of application for maximum inhibiting effect is easily achieved by one skilled in the art by evaluating the compound under conditions of use.

The test results summarized in Table D indicate that the compounds disclosed and claimed are effective against one or more classes of microorganisms. The compounds are therefore useful in inhibiting the growth of microorganisms by applying to a locus inhabited by microorganisms an antimicrobially effective amount of such compound.

The test results were obtained as follows. A representative selection of the test microorganisms were cultured in a nutrient broth, such as, for example, Eugon, commercially available from Difco Laboratories, Detroit, Michigan. Bacteria and Candida species were cultured for 24 hours at 32°–37° C. and fungi were cultured for approximately one week at 32° C. Inocula were prepared by suspending the growth or spores from a slant culture in sufficient sterile normal (0.9 percent) saline or Eugon broth, to yield cell or spore concentrations of 1,000,000 cells per milliliter. Anaerobic bacteria were cultured for 48–72 hours at 32°–37° C. in a thioglycollate containing medium, for example, Fluid Thioglycollate medium or NIH thioglycollate broth, commercially available from Difco Laboratories.

The compounds of the present invention were tested for activity against bacteria, yeasts and fungi by the agar incorporation method described below. MA 1347, 3-(dimethylaminomethyl)flavanone (disclosed in U.S. Pat. No. 3,753,985) was used as a comparative standard along with controls for each solvent system used.

A series of agar plates containing two-fold dilutions of each compound to be tested, ranging in concentration from 100 to 3.1 mcg/ml of agar medium was prepared. Aliquots of each concentration (100, 50, 25, 12.5, 6.2, and 3.1) prepared in N,N-dimethylformamide or 50 percent aqueous DMF were added to liquid Eugon agar at 48° C. (one part test solution to 100 parts agar). In some cases, tests with further dilutions to 0.125 mcg/ml were conducted. The agar medium, containing the 3-methylene flavanone or chromanone compound to be tested, was then dispensed into petri dishes and allowed to solidify. The solidified plates were kept overnight at room temperatures to dry the surface of the agar.

The agar plates were then inoculated with a drop of the standardized cell or spore suspension. Inoculated plates were incubated at 32° C. The inhibition end-point or minimum inhibitory concentration (MIC) shown in Table D represent the lowest concentration of test compound which inhibited the growth of the microorganism. Visual determination of growth inhibition was used. Bacteria and yeast end-points were determined after 24 hours incubation; molds, dermatophytes and anaerobes after 48–72 hours incubation. MIC values shown as ranges represent the extremes found in repeat assays. Virtually all such values were written plus or minus one dilution, the accepted variation of a two-fold dilution assay.

TABLE D

| | MA 1347 | TR 3489 Ex. 1 | TR 3667 Ex. 2 | TR 3498 Ex. 3 | TR 3734 Ex. 4 | TR 3673 Ex. 6 | TR 3648 Ex. 7 | TR 3762 Ex. 8 | TR 3666 Ex. 9 |
|---|---|---|---|---|---|---|---|---|---|
| Minimal Inhibitory Concentration (mcg/ml) | | | | | | | | | |
| *Staphylococcus aureus* ATCC 6538 | 6.2–12.5 | 6.2 | ≦3.1 | ≦3.1 | 1.56 | ≦3.1 | 25 | 12.5 | 6.2 |
| *S. aureus* NRRL B2747 | 6.2–12.5 | 12.5 | 6.2 | 3.1 | 1.56 | 6.2 | 25 | 12.5 | 6.2 |
| *S. aureus** NRRL B2747 | 25 | 25 | — | — | 6.2 | — | — | — | — |
| *Streptococcus faecalis* ATCC 10541 | 50 | 100 | 25 | 25 | 25–50 | 25 | 100 | >100 | 50 |
| *Sarcina subflava* ATCC 7468 | 12.5 | — | — | 6.2 | 3.1 | — | — | — | — |
| *Escherichia coli* ATCC 8739 | >100 | >100 | >100 | >100 | >100 | >100 | >100 | >100 | >100 |
| *Proteus vulgaris* NRRL B123 | >100 | — | — | >100 | — | — | — | — | — |
| *Pseudomonas aeruginosa* ATCC 14502 | >100 | >100 | >100 | >100 | >100 | >100 | >100 | >100 | >100 |
| *Bacteriodides fragilis** ATCC 8482 | 3.1 | 1.56 | — | — | 3.1 | — | — | — | — |
| *Clostridium acetobutylicum** ATCC 824 | ≦100 | — | — | ≦100 | — | — | — | — | — |
| *C. sporogenes** ATCC 11437 | 6.2 | 12.5 | — | — | ≦0.78 | — | — | — | — |
| *Propionobacterium acnes** ATCC 6919 | 12.5 | 12.5 | — | ≦100 | 3.1 | — | — | >100 | — |
| *Candida albicans* ATCC 10231 | 25–50 | 50 | 25 | 12.5 | 25 | 25 | >100 | 100 | 50 |
| *C. albicans* NRRL Y-477 | 25 | 50 | 25 | 12.5 | 25 | 25 | 100 | 100 | 50 |
| *C. krusei* VM 29B | 12.5–25 | 50 | 25 | 12.5 | 25–50 | 25 | 100 | 50 | 50 |
| *C. tropicalis* NRRL Y1410 | 50–100 | 100 | 50 | 25 | 50 | 25 | >100 | >100 | 50 |
| *C. guillermondii* VM 42 | 50–100 | 100 | 50 | 25 | 50 | 25 | >100 | 100 | 100 |
| *Trichophyton mentagrophytes* ATCC 4807 | 6.2–12.5 | 12.5 | 6.2 | 6.2 | 12.5 | 6.2 | 25 | 12.5 | 12.5 |
| *T. mentagrophytes* TM-2 | 6.2–12.5 | 12.5 | 6.2 | 6.2 | 12.5–25 | 6.2 | 25 | 12.5 | 6.2 |
| *T. mentagrophytes* CDC | 6.2–12.5 | 12.5 | 12.5 | 6.2 | 12.5–25 | 12.5 | 25 | 12.5 | 12.5 |
| *T. tonsurans* ATCC 10217 | 6.2 | 6.2 | — | — | 6.2 | — | — | — | — |
| *T. rubrum* ATCC 10218 | ≦3.1–12.5 | — | ≦3.1 | ≦3.1 | 12.5 | 6.2 | 12.5 | 25 | 6.2 |

TABLE D-continued

| | | | | | | | | | |
|---|---|---|---|---|---|---|---|---|---|
| *Microsporum gypseum* ATCC 14682 | 6.2–12.5 | 6.2–12.5 | 6.2 | 6.2 | 6.2–12.5 | 6.2 | 25 | 12.5 | 6.2 |
| *Aspergillus niger* ATCC 16404 | 50 | 100->100 | 100 | 25 | 100 | 50 | >100 | 100 | 50 |
| *A. fumigatus* NRRL 163 | 6.2–25 | 6.2 | — | 6.2 | 50 | — | — | 50 | — |
| *A. fumigatus* NRRL 165 | 50->100 | — | 100 | 50 | — | 50 | >100 | — | 100 |

| | MA 1347 | TR 3614 Ex. 10 | TR 3654 Ex. 11 | TR 3485 Ex. 13 | TR 3683 Ex. 14 | TR 3649 Ex. 16 | TR 3791 Ex. 17 | TR 3782 Ex. 18 | TR 3783 Ex. 19 |
|---|---|---|---|---|---|---|---|---|---|
| *Staphylococcus aureus* ATCC 6538 | 6.2–12.5 | ≦3.1 | 50 | 6.2 | ≦3.1 | 12.5 | 6.2 | ≦3.1 | 6.2 |
| *S. aureus* NRRL B2747 | 6.2–12.5 | 6.2 | 50 | 6.2 | ≦3.1–6.2 | 12.5 | 12.5 | 6.2 | 6.2 |
| *S. aureus\** NRRL B2747 | 25 | — | — | — | — | — | — | — | — |
| *Streptococcus faecalis* ATCC 10541 | 50 | 50 | >100 | 50 | 25–50 | 100 | >100 | 50 | 50 |
| *Sarcina subflava* ATCC 7468 | 12.5 | 12.5 | — | 12.5 | — | — | — | — | — |
| *Escherichia coli* ATCC 8739 | >100 | >100 | >100 | >100 | >100 | >100 | >100 | >100 | >100 |
| *Proteus vulgaris* NRRL B123 | >100 | >100 | — | >100 | — | — | — | — | — |
| *Pseudomonas aeruginisa* ATCC 14502 | >100 | >100 | >100 | >100 | >100 | >100 | >100 | >100 | >100 |
| *Bacteriodides fragilis\** ATCC 8482 | 3.1 | — | — | — | — | — | — | — | — |
| *Clostridium acetobutylicum\** ATCC 824 | ≦100 | ≦100 | — | ≦100 | — | — | — | — | — |
| *C. sporogenes\** ATCC 11437 | 6.2 | — | — | — | — | — | — | — | — |
| *Propionobacterium acnes\** ATCC 6919 | 12.5 | ≦100 | — | ≦100 | ≦100 | — | — | ≦100 | ≦100 |
| *Candida albicans* ATCC 10231 | 25–50 | 25 | >100 | 25 | 50->100 | 50 | 100 | 50 | 25 |
| *C. albicans* NRRL Y-477 | 25 | 25 | >100 | 25 | 50->100 | 50 | 100 | 50 | 25 |
| *C. krusei* VM 29B | 12.5–25 | 25 | 100 | 25 | 50 | 50 | 100 | 25 | 25 |
| *C. tropicalis* NRRL Y1410 | 50–100 | 50 | >100 | 50 | >100 | 50 | >100 | >100 | 25 |
| *C. guillermondii* VM 42 | 50–100 | 50 | >100 | 50 | >100 | 100 | >100 | >100 | 25 |
| *Trichophyton mentagrophytes* ATCC 4807 | 6.2–12.5 | 6.2 | 25 | 6.2 | 25 | 12.5 | 12.5 | 12.5 | 6.2 |
| *T. mentagrophytes* TM-2 | 6.2–12.5 | 6.2 | 25 | 6.2 | 25 | 12.5 | 25 | 12.5 | 6.2 |
| *T. mentagrophytes* CDC | 6.2–12.5 | 6.2 | 25 | 6.2 | 25 | 25 | 50 | 12.5 | 6.2 |
| *T. tonsurans* ATCC 10217 | 6.2 | — | — | — | — | — | — | — | — |
| *T. rubrum* ATCC 10218 | ≦3.1–12.5 | ≦3.1 | 12.5 | ≦3.1 | 12.5–25 | 6.2 | 25 | 12.5 | 6.2 |
| *Microsporum gypseum* ATCC 14683 | 6.12–12.5 | 6.2 | 25 | 6.2 | 12.5–25 | 12.5 | 50 | 6.2 | 6.2 |
| *Aspergillus niger* ATCC 16404 | 50 | 50 | >100 | 50 | 100 | 50 | >100 | 25 | 25 |
| *A. fumigatus* NRRL 163 | 5.2–25 | 12.5 | — | 12.5 | 50->100 | — | >100 | 12.5 | 25 |
| *A. fumigatus* NRRL 165 | 50->100 | 100 | >100 | 50 | — | 100 | >100 | — | — |

| | MA 1347 | TR 3742 Ex. 20 | TR 3928 Ex. 21 | TR 3927 Ex. 22 | TR 3659 Ex. 23 | TR 3658 Ex. 24 |
|---|---|---|---|---|---|---|
| *Staphylococcus aureus* ATCC 6538 | 6.2–12.5 | 0.5 | 0.5 | 0.78 | ≦3.1 | ≦3.1 |
| *S. aureus* NRRL B2747 | 6.2–12.5 | 0.25–0.5 | 0.5 | 0.78 | 6.2 | 6.2 |
| *S. aureus\** NRRL B2747 | 25 | 0.25–1.0 | 1.56 | 1.0 | — | — |
| *Streptococcus faecalis* ATCC 10541 | 50 | 0.78–1.0 | 1.0 | 3.1 | 50 | 50 |
| *Sarcina subflava* ATCC 7468 | 12.5 | 1.0 | 1.56 | 3.1 | — | — |
| *Escherichia coli* ATCC 8739 | >100 | >100 | >100 | >100 | >100 | >100 |
| *Proteus vulgaris* NRRL B123 | >100 | >100 | — | — | — | — |
| *Pseudomonas aeruginosa* ATCC 14502 | >100 | >100 | >100 | >100 | >100 | >100 |

TABLE D-continued

| | | | | | | |
|---|---|---|---|---|---|---|
| *Bacteriodides fragilis* * ATCC 8482 | 3.1 | 0.125 | 0.25 | 0.25 | — | — |
| *Clostridium acetobutylicum* * ATCC 824 | <100 | 1.0 | — | — | — | — |
| *Clostridium sporogenes* * ATCC 11437 | 6.2 | 0.5 | 0.5 | 0.5 | — | — |
| *Propionobacterium acnes* * ATCC 6919 | 12.5 | 0.78–3.1 | 1.0 | 1.0 | — | — |
| *Candida albicans* ATCC 10231 | 25–50 | >100 | >100 | 100 | >100 | >100 |
| *C. albicans* NRRL Y-477 | 25 | >100 | >100 | 100 | 100 | 100 |
| *C. krusei* VM 29B | 12.5–25 | >100 | >100 | 100 | 50 | 25 |
| *C. tropicalis* NRRL Y1410 | 50–100 | >100 | >100 | >100 | >100 | >100 |
| *C. guillermondii* VM 42 | 50–100 | >100 | >100 | >100 | >100 | >100 |
| *Trichophyton mentagrophytes* ATCC 4807 | 6.2–12.5 | >100 | 12.5 | 12.5 | 6.2 | 12.5 |
| *T. mentagrophytes* TM-2 | 6.2–12.5 | >100 | 12.5 | 12.5 | 12.5 | 12.5 |
| *T. mentagrophytes* CDC | 6.2–12.5 | >100 | 12.5 | 25 | 12.5 | 25 |
| *T. tonsurans* ATCC 10217 | 6.2 | >100 | 6.2 | 6.2 | — | — |
| *T. rubrum* ATCC 10218 | <3.1–12.5 | >100 | — | — | 6.2 | 6.2 |
| *Microsporum gypseum* ATCC 14683 | 6.2–12.5 | <3.1–>100 | 6.2 | 12.5 | 6.2 | 12.5 |
| *Aspergillus niger* ATCC 16404 | 50 | >100 | >100 | >100 | >100 | >100 |
| *A. fumigatus* NRRL 163 | 6.2–25 | >100 | 100 | 25 | — | — |
| *A. fumigatus* NRRL 165 | 50–>100 | >100 | — | — | >100 | >100 |

*Anaerobic: 48 hours incubation at 35° C. Gas-Pak Anaerobic Jar

Compounds which compare preferred embodiments of Formula III, Examples 20–22, wherein R is phenyl showed increased potency against gram positive microorganisms, e.g., staphylococcus and streptococcus microorganisms.

What is claimed is:

1. A compound of the formula:

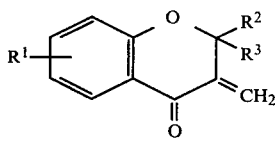

and pharmacologically acceptable, non-toxic salts thereof wherein:

$R^1$ is a member selected from the group consisting of hydrogen, Br, $CH_3$ and $OCH_3$;

$R^2$ is selected from the group consisting of hydrogen and

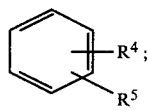

wherein $R^4$ is a member selected from the group consisting of hydrogen, Br, Cl, $CH_3$, $OCH_3$, $NO_2$, $N(CH_3)_2$, $C(CH_3)_3$ and CN; $R^5$ is selected from the group consisting of hydrogen and Cl, with the proviso that when $R^5$ is Cl, $R^4$ is hydrogen or Cl; and $R^3$ is selected from the group consisting of hydrogen, phenyl, 2-thienyl, 4-pyridyl and naphthyl, with the proviso that when $R^3$ is naphthyl, $R^1$ and $R^2$ are hydrogen.

2. A compound as claimed in claim 1 wherein $R^2$ is

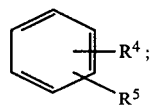

and $R^3$ and $R^5$ are hydrogen.

3. A compound as claimed in claim 2 wherein $R^1$ is hydrogen.

4. A compound as claimed in claim 3 wherein $R^4$ is hydrogen.

5. A compound as claimed in claim 3 wherein $R^4$ is Cl.

6. A compound as claimed in claim 3 wherein $R^4$ is Br.

7. A compound as claimed in claim 3 wherein $R^4$ is $OCH_3$.

8. A compound as claimed in claim 3 wherein $R^4$ is $NO_2$.

9. A compound as claimed in claim 3 wherein $R^4$ is $N(CH_3)_2$.

10. A compound as claimed in claim 3 wherein $R^4$ is $CH_3$.

11. A compound as claimed in claim 3 wherein $R^4$ is $C(CH_3)_3$.

12. A compound as claimed in claim 3 wherein $R^4$ is CN.

13. A compound as claimed in claim 1 wherein $R^1$, $R^3$ and $R^4$ are hydrogen; $R^2$ is

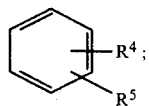

and $R^5$ is Cl.

14. A compound as claimed in claim 1 wherein $R^1$ and $R^3$ are hydrogen; $R^2$ is

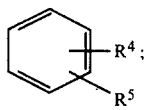

and $R^4$ and $R^5$ are Cl.

15. A compound as claimed in claim 2 wherein $R^1$ and $R^4$ are Br.

16. A compound as claimed in claim 2 wherein $R^1$ is $OCH_3$ and $R^4$ is Cl.

17. A compound as claimed in claim 2 wherein $R^1$ is $CH_3$ and $R^4$ is hydrogen.

18. A compound as claimed in claim 1 wherein $R^1$, $R^4$ and $R^5$ are hydrogen; $R^2$ is

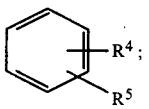

and $R^3$ is selected from the group consisting of phenyl, 2-thienyl and 4-pyridyl.

19. A compound as claimed in claim 18 wherein $R^3$ is phenyl.

20. A compound as claimed in claim 18 wherein $R^3$ is 2-thienyl.

21. A compound as claimed in claim 18 wherein $R^3$ is 4-pyridyl.

22. A compound as claimed in claim 1 wherein $R^1$ and $R^2$ are hydrogen; and $R^3$ is naphthyl.

23. A method for inhibiting the growth of microorganisms which comprises applying to the locus to be inhibited an antimicrobially effective amount of a compound having the structural formula:

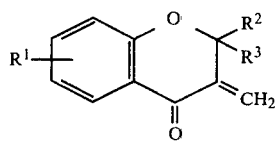

and pharmacologically acceptable, non-toxic salts thereof wherein:

$R^1$ is a member selected from the group consisting of hydrogen, Br, $CH_3$ and $OCH_3$;

$R^2$ is selected from the group consisting of hydrogen and and

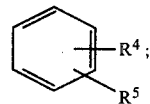

wherein $R^4$ is a member selected from the group consisting of hydrogen, Br, Cl, $CH_3$, $OCH_3$, $NO_2$, $N(CH_3)_2$, $C(CH_3)_3$ and CH; $R^5$ is selected from the group consisting of hydrogen and Cl, with the proviso that when $R^5$ is Cl, $R^4$ is hydrogen or Cl; and $R^3$ is selected from the group consisting of hydrogen, phenyl, 2-thienyl, 4-pyridyl and naphthyl, with the proviso that when $R^3$ is naphthyl, $R^1$ and $R^2$ are hydrogen.

24. A method as claimed in claim 23 wherein $R^2$ is

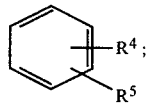

and $R^3$ and $R^5$ are hydrogen.

25. A method as claimed in claim 23 wherein $R^1$, $R^4$ and $R^5$ are hydrogen; $R^2$ is

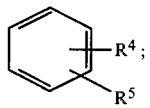

and $R^3$ is selected from the group consisting of phenyl, 2-thienyl and 4-pyridyl.

26. A method as claimed in claim 23 wherein $R^1$ and $R^2$ are hydrogen; and $R^3$ is naphthyl.

* * * * *

UNITED STATES PATENT AND TRADEMARK OFFICE
CERTIFICATE OF CORRECTION

PATENT NO. : 4,241,069

DATED : December 23, 1980

INVENTOR(S) : Robert T. Buckler, Frederick E. Ward and David L. Garling

It is certified that error appears in the above-identified patent and that said Letters Patent are hereby corrected as shown below:

In the abstract, the paragraph below the second drawing, "consisting of hydrogen, Br, Cl, $CH_3$, $OCH_3$, $NO_2$, $N(CH_3)_3$ and CN;" should read --consisting of hydrogen, Br, Cl, $CH_3$, $OCH_3$, $NO_2$, $N(CH_3)_2$, $C(CH_3)_3$ and CN; --.

Column 22, line 25, "$N(CH_3)_2$, $C(CH_3)_3$ and CH;" should read -- $N(CH_3)_2$, $C(CH_3)_3$ and CN; --.

Signed and Sealed this

Fifteenth Day of December 1981

|SEAL|

Attest:

GERALD J. MOSSINGHOFF

Attesting Officer

Commissioner of Patents and Trademarks